(12) United States Patent
Novak et al.

(10) Patent No.: US 10,039,510 B2
(45) Date of Patent: Aug. 7, 2018

(54) VISUALIZING DIFFERENT TYPES OF AIRWAY WALL ABNORMALITIES

(71) Applicant: Siemens Healthcare GmbH, Erlangen (DE)

(72) Inventors: Carol Novak, Newtown, PA (US); Benjamin Odry, West New York, NJ (US); Atilla Kiraly, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 72 days.

(21) Appl. No.: 15/238,722

(22) Filed: Aug. 17, 2016

(65) Prior Publication Data

US 2017/0079603 A1    Mar. 23, 2017

Related U.S. Application Data

(60) Provisional application No. 62/221,700, filed on Sep. 22, 2015.

(51) Int. Cl.
*A61B 6/00* (2006.01)
*A61B 6/03* (2006.01)
(Continued)

(52) U.S. Cl.
CPC .............. *A61B 6/482* (2013.01); *A61B 6/032* (2013.01); *A61B 6/50* (2013.01); *A61B 6/5223* (2013.01);
(Continued)

(58) Field of Classification Search
CPC ... G06K 9/4604; G06T 7/0012; G06T 7/0081; G06T 11/008; G06T 2207/10081;
(Continued)

(56) References Cited

U.S. PATENT DOCUMENTS

2005/0105788 A1* 5/2005 Turek ............... G06F 19/321
                                                         382/131
2007/0071301 A1* 3/2007 Kiraly ................. G06T 7/11
                                                         382/131
(Continued)

OTHER PUBLICATIONS

Mumcuoglu et al. "Image Analysis for Cystic Fibrosis: Automatic Lung Airway Wall and Vessel Measurement on CT Images." Annual International Conference of the IEEE Engineering in Medicine and Biology Society, Sep. 3, 2009, pp. 3545-3548.*
(Continued)

*Primary Examiner* — Jon Chang

(57) ABSTRACT

A method for visualizing airway wall abnormalities includes acquiring\Dual Energy Computed Tomography (DECT) imaging data comprising one or more image volumes representative of a bronchial tree. An iodine map is derived using the DECT imaging data and the bronchial tree is segmented from the image volume(s). A tree model representative of the bronchial tree is generated. Then, for each branch, this tree model is used to determine an indicator of normal or abnormal thickness. Locations corresponding to bronchial walls in the bronchial tree using the tree model are identified. Next, for each branch, the locations corresponding to bronchial walls in the bronchial tree and the iodine map are used to determine an indicator of normal or abnormal inflammation. A visualization of the bronchial tree may be presented with visual indicators at each of the locations corresponding to bronchial walls indicating whether a bronchial wall is thickened and/or inflamed.

22 Claims, 5 Drawing Sheets

(51) Int. Cl.
  *G06K 9/46* (2006.01)
  *G06T 7/00* (2017.01)
  *G06T 11/00* (2006.01)
(52) U.S. Cl.
  CPC .......... *G06K 9/4604* (2013.01); *G06T 7/0012* (2013.01); *G06T 7/0081* (2013.01); *G06T 11/008* (2013.01); *G06T 2207/10081* (2013.01); *G06T 2207/30061* (2013.01); *G06T 2207/30101* (2013.01); *G06T 2211/408* (2013.01)
(58) Field of Classification Search
  CPC . G06T 2207/30061; G06T 2207/30101; G06T 2211/408; A61B 6/482; A61B 6/032; A61B 6/50; A61B 6/5223
  See application file for complete search history.

(56) References Cited

U.S. PATENT DOCUMENTS

| | | | | |
|---|---|---|---|---|
| 2011/0071383 | A1* | 3/2011 | Novak | A61B 5/1075 600/416 |
| 2015/0086099 | A1 | 3/2015 | Kiraly et al. | |
| 2015/0351714 | A1* | 12/2015 | De Backer | A61B 5/085 600/427 |

OTHER PUBLICATIONS

Zhou et al. "NIR Fluorescent Contrast Agents for Detection of Inflammation of Lungs in vivo." Conference on Lasers and Electro-Optics, Jun. 8, 2014, 2 pages.*

Geng et al. "Fast 3D Skeleton Extraction of Airways and Applications to Virtual Bronchoscopy." The 26th Chinese Control and Decision Conference, May 31, 2014, pp. 3879-3884.*

Fetita et al. "Pulmonary Airways: 3-D Reconstruction from Multislice CT and Clinical Investigation." IEEE Trans. Medical Imaging, vol. 23, No. 11, Nov. 2004, pp. 1353-1364.*

Kiraly et al. "Three-Dimensional Path Planning for Virtual Bronchoscopy." IEEE Transactions on Medical Imaging, vol. 23, No. 9, Sep. 2004, pp. 1365-1379.*

Odry et al. "Active Contour Approach for Accurate Quantitative Airway Analysis." Proceedings of the SPIE 6916, Medical Imaging 2008: Physiology, Function, and Structure from Medical Images, 691613, Mar. 12, 2008, 11 pages.*

Kiraly et al. "Boundary-Specific Cost Functions for Quantitative Airway Analysis." Medical Image Computing and Computer Assisted Intervention (MICCAI), Part I, LNCS, 3791, 2007, pp. 784-791.*

Odry et al. "An Evaluation of Automated Broncho-arterial Ratios for Reliable Assessment of Bronchiectasis." Proceedings of the SPIE 6915, Medical Imaging 2008: Computer-Aided Diagnosis, Mar. 17, 2008, 9 pages.*

Kiraly et al. "Three-dimensional Human Airway Segmentation Methods for Clinical Virtual Bronchoscopy." Academic Radiology, 9(10), 2002, pp. 1153-1168.*

Benjamin L. Odry et al: "Quantitative evaluation of bronchial enhancement: preliminaryobservations", Optical Sensing 11, vol. 7626, p. 76260Z, Mar. 4, 2010.

* cited by examiner

| Thickening value $t_b$ | Inflammation value $i_b$ | |
|---|---|---|
| | 1 | 0 |
| 1 | Both thickened and inflamed [red] | Thickened but not inflamed [green] |
| 0 | Inflamed but not thickened [yellow] | Normal [blue] |

*Fig. 4*

VISUALIZING DIFFERENT TYPES OF AIRWAY WALL ABNORMALITIES

CROSS-REFERENCE TO RELATED APPLICATIONS

This application claims the benefit of U.S. Provisional Application Ser. No. 62/221,700 filed Sep. 22, 2015 which is incorporated herein by reference in its entirety.

TECHNICAL FIELD

The present invention relates generally to methods, systems, and apparatuses for visualizing different types of airway wall abnormalities. The techniques described herein may be applied, for example, in the clinical diagnosis of pulmonary disease.

BACKGROUND

Pulmonary diseases such as bronchiectasis, asthma, cystic fibrosis and Chronic Obstructive Pulmonary Disease (COPD) are characterized by abnormalities in airway dimensions, including airway wall thickness and lumen size (inner airway). Computed Tomography (CT) has become one of the primary means to depict and detect these abnormalities, as the availability of high-resolution near-isotropic data makes it possible to evaluate airways at oblique angles to the scanner plane. However, currently, clinical evaluation of airways is typically limited to subjective visual inspection only; systematic evaluation of the airways to take advantage of high-resolution data has not proved practical without automation.

Recently, automated methods have been proposed that are based on automatic extraction and modeling of the airway tree. After a tree model is obtained, an automated method can generate measurements of the airway dimensions, including wall thickness. The results can be classified as normal or abnormal. After this has been done, a model of the tree can be colored to depict normal and abnormal bronchi, or to depict severity. As a result, a 3D view of the bronchial tree can be created that has differing colorings for thickened walls vs. normal walls.

However, airway walls may be thicker due to inflammatory disease processes or to other processes such as scarring. Furthermore, inflammatory causes of thickening may be potentially treatable (such as with anti-inflammatory agents) whereas scarring type processes are less likely to respond to treatment. Hence it would be valuable to know whether observed wall thickening is due to an inflammatory process, in order to better individualize patient treatment.

In previous experiments, it was shown that some airway walls in patients with airway disease experience iodine uptake following the administration of intravenous iodinated contrast. This iodine uptake in bronchial walls is believed to be caused by an increase in local blood flow, which in turn is caused by inflammation. Furthermore our experiments have also shown that the amount of iodine uptake may be estimated with Dual Energy Computed Tomography (DECT) imaging. The result of DECT imaging is an iodine map that depicts the amount of iodine uptake at any given location in the volume. Given a segmentation of the bronchial walls, a 3D view of the bronchial tree can be created that has differing colors for high uptake vs. low uptake amounts.

The challenge for physicians is to (1) rapidly identify thickened airway walls; and (2) distinguish thickened walls with high iodine uptake—indicating inflammatory disease—from those with little to no iodine—indicating non-inflammatory thickening. Accordingly, it is desired to provide a system for an interactive user interface that allows physicians to make just such a distinction.

SUMMARY

Embodiments of the present invention address and overcome one or more of the above shortcomings and drawbacks, by providing methods, systems, and apparatuses related to visualizing different types of airway wall abnormalities. Briefly, the techniques described herein may be applied to detect airways that are (i) thickened but not inflamed; (ii) both thickened and inflamed; (iii) inflamed but not thickened; or (iv) normal. This information may then be used to provide visual indicators of disease through multiple interactive displays. For example, in some embodiments, voxels corresponding to the detected bronchial wall locations have a semi-transparent overlay of a color indicating its corresponding thickness and/or inflammation values.

According to some embodiments, a computer-implemented method for visualizing airway wall abnormalities includes acquiring a Dual Energy Computed Tomography (DECT) imaging data comprising one or more image volumes representative of a bronchial tree. An iodine map is derived using the DECT imaging data and the bronchial tree is segmented from the one or more image volumes. A tree model representative of the bronchial tree is generated. Then, for each branch, this tree model is used to determine an indicator of normal or abnormal thickness for the branch. The indicator of normal or abnormal thickness for the branch is a binary indicator, or this indicator may provide an indication of degrees of thickening on the branch. Locations corresponding to bronchial walls in the bronchial tree using the tree model are identified. Next, for each branch, the locations corresponding to bronchial walls in the bronchial tree and the iodine map are used to determine an indicator of normal or abnormal inflammation as measured by iodine uptake on the branch. As with the thickness indicator, the indicator of normal or abnormal inflammation for the branch is a binary indicator or it may provide an indication of degrees of thickening on the branch.

After performing the aforementioned method, a visualization of the bronchial tree may be presented with visual indicators at each of the locations corresponding to bronchial walls indicating whether a bronchial wall is thickened, inflamed, or both thickened and inflamed. In some embodiments, the visualization comprises a Multi-Planar Reconstruction from the DECT imaging data and the visual indicators comprise semi-transparent overlay colors distinguishing between thickened walls with and without inflammation in the bronchial tree. In other embodiments, the visualization comprises a 3D visualization of the bronchial tree and the visual indicators comprise colors distinguishing between thickened walls with and without inflammation in the bronchial tree. In one embodiment, the visualization further comprises one or more interactive interface components that, when activated, cause the visualization to provide a series of visualizations corresponding to a list of airways that exhibit at least one of thickening or inflammation.

In some embodiments of the aforementioned method, the tree model is used to determine the indicator of normal or abnormal thickness for the branch by using the tree model to segment inner and outer walls of each airway in the bronchial tree; computing local wall thickness for each airway based on the airway's corresponding inner and outer walls;

and computing an overall wall thickness for each branch of the bronchial tree based on the local wall thickness computed for each airway. Then, for each branch, the overall wall thickness is used across the branch to determine the indicator of normal or abnormal thickness for the branch. The overall wall thickness may comprise a mean wall thickness computed using the local wall thickness computed for each airway or, alternatively, the maximum wall thickness among the local wall thickness computed for each airway. In one embodiment, each branch in the tree model corresponds to a generation number and the indicator of normal or abnormal thickness for the branch is determined by designating the branch as having abnormal thickness if the overall wall thickness is above a predetermined threshold value corresponding to the generation number. In some embodiments, the indicator of normal or abnormal thickness for the branch is determined by identifying an artery that is adjacent to the branch using the DECT imaging data and determining the diameter of the artery. The overall wall thickness is divided across the branch by the diameter of the artery to yield a ratio for the branch. The branch may then be designated as having abnormal thickness if the ratio is above a predetermined threshold value.

Some embodiments of the aforementioned method process each branch in the tree model by determining a set of points form a centerline for the branch and computing inner and outer airway wall contours at each point on the centerline of the branch. Then, voxels in the DECT imaging data that fall between the inner and outer airway wall contours may be designated as the locations corresponding to bronchial walls in the bronchial tree.

According to other embodiments, a system for visualizing airway wall abnormalities comprises a CT imaging scanner, a display, and a computing device comprising one or more processors and a non-transitory, computer-readable storage medium in operable communication with the processors. The CT imaging scanner is configured to acquire DECT imaging data comprising one or more image volumes representative of a bronchial tree. The computer-readable storage medium comprises one or more programming instructions that, when executed, cause the processors to derive an iodine map using the DECT imaging data, segment the bronchial tree from the one or more image volumes, and generate a tree model representative of the bronchial tree. Additionally, these instructions cause the processors to use the tree model to determine an indicator of normal or abnormal thickness for each branch and identify locations corresponding to bronchial walls in the bronchial tree using the tree model. The instructions also cause the processors to use the locations corresponding to bronchial walls in the bronchial tree and the iodine map to determine an indicator of normal or abnormal inflammation as measured by iodine uptake on each branch. A visualization of the bronchial tree may be presented on the display with visual indicators at each of the locations corresponding to bronchial walls indicating whether a bronchial wall is thickened, inflamed, or both thickened and inflamed. The features of the system may be supplemented, refined or enhanced using any of the methods discussed above with respect to the aforementioned computer-implemented method for visualizing airway wall abnormalities.

According to other embodiments of the present invention, a system for visualizing airway wall abnormalities comprises a database and a parallel computing environment. The database stores CT imaging data comprising one or more image volumes representative of a bronchial tree. T parallel computing environment comprises a plurality of processors that are configured to generate a model of the bronchial tree based on the one or more image volumes and, in parallel for each branch of the bronchial tree, use the model of the bronchial tree to determine (a) an indicator of normal or abnormal thickness for the branch and (b) an indicator of normal or abnormal inflammation for the branch. The processors may be further configured to present a visualization of the bronchial tree on the display with visual indicators at each locations corresponding to bronchial walls indicating whether a bronchial wall is thickened, inflamed, or both thickened and inflamed based on the indicator of normal or abnormal thickness and the indicator of normal or abnormal inflammation determined for each branch.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 4 provides an example of the color display map that may be employed in some embodiments to distinguish between thickened walls with and without inflammation.

DETAILED DESCRIPTION

The following disclosure describes the present invention according to several embodiments directed at methods, systems, and apparatuses related to visualizing different types of airway wall abnormalities The techniques described herein may be used to automatically compute and display the locations of airways that are (i) thickened but not inflamed; (ii) both thickened and inflamed; (iii) inflamed but not thickened; or (iv) normal. Any abnormalities that are detected may be presented in an interactive display that allows physicians to rapidly identify these different types of abnormalities. Such a display gives the physician the ability to distinguish between thickened walls that have inflammation—and are potentially treatable with anti-inflammatory drugs—from thickened walls without inflammation, which have a less hopeful prognosis.

Figure 1:
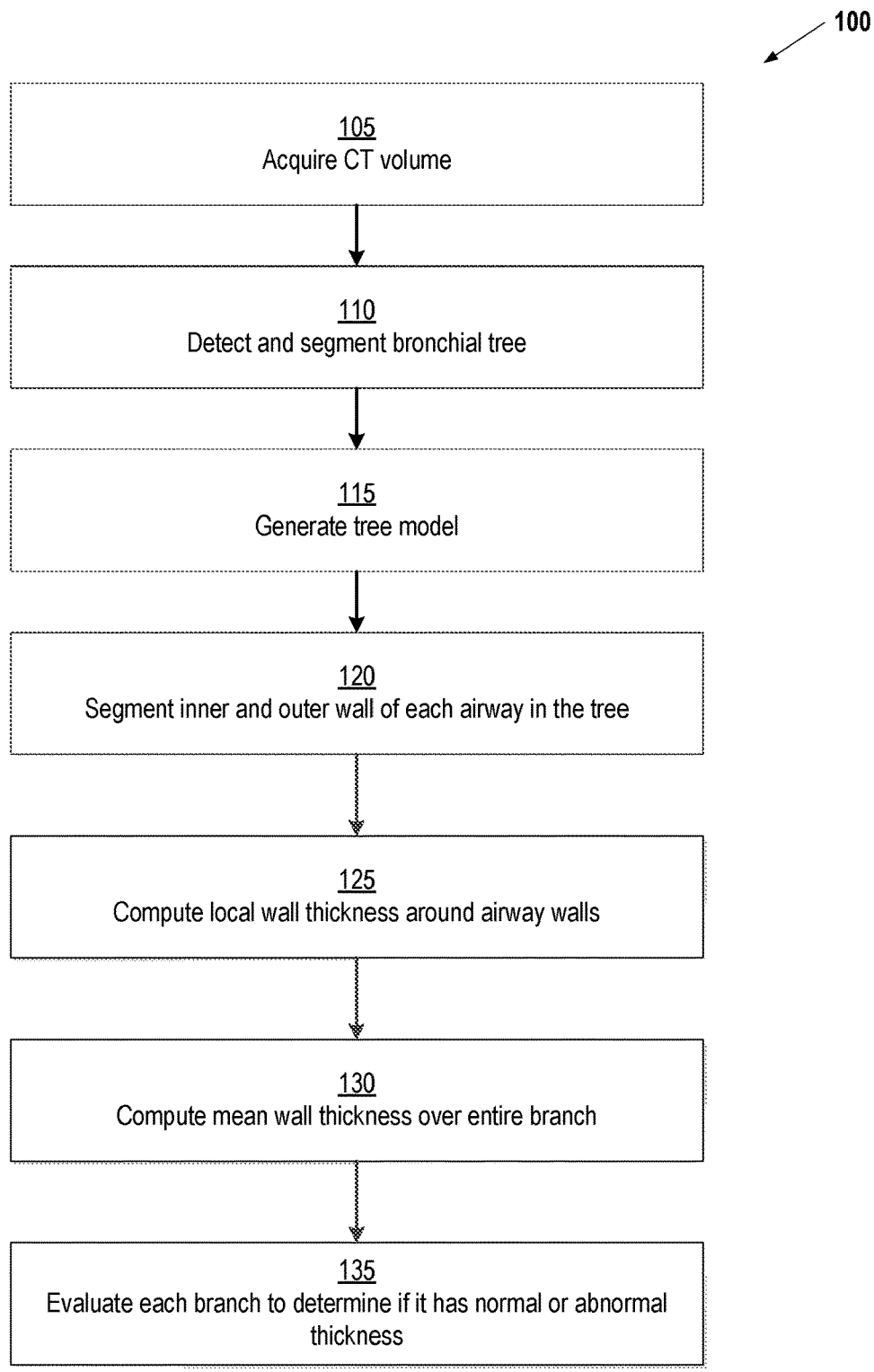
FIG. 1 presents a method for detecting thickened bronchial walls, according to some embodiments.

FIG. 1 presents a method 100 for detecting thickened bronchial walls, according to some embodiments. The method begins at step 105 by acquiring a CT volume of the patient's lungs. Next, at step 110, the bronchial tree is automatically detected and segmented from the image acquired at step 105. Any technique generally known in the art may be used to perform the detection and segmentation at step 110. For example, in one embodiment, a region growing technique is used where voxels with gray values within a particular threshold interval and connected to a seed point are segmented into the tree structure.

Once the bronchial tree is segmented, at step 115, skeletonization and further post-processing is performed to create a tree model T defined by the set of branches B that form the tree, proceeding from the trachea to the most distal branch extracted. The model T=(S, B, P) comprises a series of sites S, branches B, and paths P. Each site s∈S identifies a 3D location within the image as well as a heading direction for the branch to which it belongs. The tree extraction routine performed at step 115 determines for each branch b∈B the set of points that form its centerline, indicated by the XYZ coordinates in the original CT volume acquired at step 105. Branches have parent and child branches that describe the hierarchy of the tree. The trachea is the $0^{th}$ branch without parent branches. The most distal branches have no child branches. Each branch also has a generation number, computed from how many parent branches need to be traversed to reach the trachea. The trachea is generation 0, the left and right main branches are generation 1, the lobar branches are generation 2, segmental branches are generation 3, and so forth. Terminal branches are the "leaves" of the tree with no further child branches. A path is a series of connected branches.

Next, at step 120, given the segmentation of the airway tree, the inner and outer wall of each airway in the tree are automatically segmented. Various techniques generally known in the art may be applied at step 120. Representative methods for providing reliable measurements of the inner and outer walls of the airways include those described in (1) "Boundary-Specific Cost Functions for Quantitative Airway Analysis," *Med. Image Comput. Comput. Assist. Interv.* 2007, 10 (Pt. 1), 784-791; and (2) "Active contour approach for accurate quantitative airway analysis," in *SPIE Proceedings Vol. 6916: Medical Imaging* 2008: *Physiology, Function, and Structure from Medical Images,* 691613 (12 Mar. 2008) (eds. Xiaoping P. Hu; Anne V. Clough). For example, the full-width half maximum approach gauges the location of the airway wall based on half the intensity value of the maximum and minimum gray levels along a sampling direction in order to determine (a) the inner contour defining the division between the lumen and the inner surface of the airway wall and (b) the outer contour defining the division between the outer surface of the airway wall and the lung parenchyma.

Continuing with reference to FIG. 1, at step 125, for each point in a branch b∈B, the local wall thickness w of the airway wall around that point is computed using the plane perpendicular to the centerline. Given the local wall thickness w associated with each centerline point of the branch, the mean wall thickness over the entire branch $w_b$ is computed at step 130. In some embodiments, rather than the mean function, the value of $w_b$ may be computed from the median, maximum, weighted average, or other function of the values along the centerline.

At step 135, each branch is evaluated to determine whether it has normal or abnormal thickness. In a normal patient, the thickness of airway walls will decrease as the generation increases. In other words, the expected wall thickness of branches in a healthy patient differs between generation 3 (segmental branches) and generation 5 (sub-sub-segmental branches). For example, a mean wall thickness of 1 mm may be perfectly normal for generation 3 branches, while at the same time would indicate abnormal thickening for generation 5 and higher. Thus a single cut-off value to detect abnormally thickened walls will not give the best results. Instead, a table is employed that specifies the upper limit of normal wall thickness at each generation. Then, for each branch an indicator $t_b$ is computed to indicate whether it has normal or abnormal thickness. Various indicators may be used to represent thickness. For example, in some embodiments, this indicator is binary, while in other embodiments, the indicator may be adapted to indicate degrees of thickening (e.g., indicating a range from "slightly thickened" to "extremely thickened").

Figure 2:
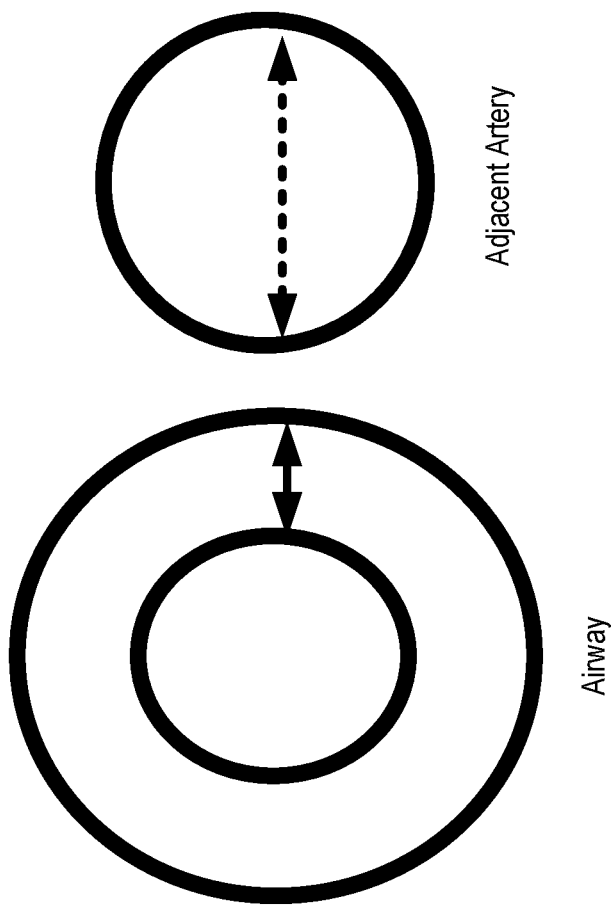
FIG. 2 provides an illustration of the ratio principle for identifying abnormally thickened walls.

In an alternative embodiment, the accompanying artery to a branch may be used to determine whether an airway wall is abnormally thick. Just as wall thickness decreases with generation number in healthy patients, so too does the diameter of the artery that parallels each airway. Rather than rely on the generation number, which can be inaccurate in the case of false branches in parent generations, comparison with the adjacent artery can use an absolute ratio to determine whether an airway wall is thickened. Current clinical practice for evaluating airway walls suggests that the wall thickness should be no larger than 15% of the diameter of the adjacent artery. FIG. 2 provides an illustration of the ratio principle for identifying abnormally thickened walls. The thickness of the airway wall (represented by a solid line) should be no larger than 15% of the diameter of the adjacent artery (represented by a dotted line).

Various techniques known in the art may be used to automatically detect the adjacent artery to a given branch and compute its diameter $d_A$. Examples of suitable techniques are described in U.S. Pat. No. 8,422,748 issued Apr. 16, 2013 and entitled "System and method for grouping airways and arteries for quantitative analysis," the entirety of which is incorporated herein by reference. Additional examples are described in "An evaluation of automated broncho-arterial ratios for reliable assessment of bronchiectasis", SPIE Medical Imaging 2008, Proceedings of the SPIE Vol. 6915, p. 69152M, 2008. The mean wall thickness $w_b$ is divided by the artery diameter $d_A$ to yield the ratio $r_b$ for each branch. Values above a set threshold (such as 0.25) may be identified as abnormal to set the value of the binary indicator $t_b$. Alternatively the indicator can take on a range of values, in order to differentiate ratios slightly above the threshold from values greatly above the threshold.

Figure 3:
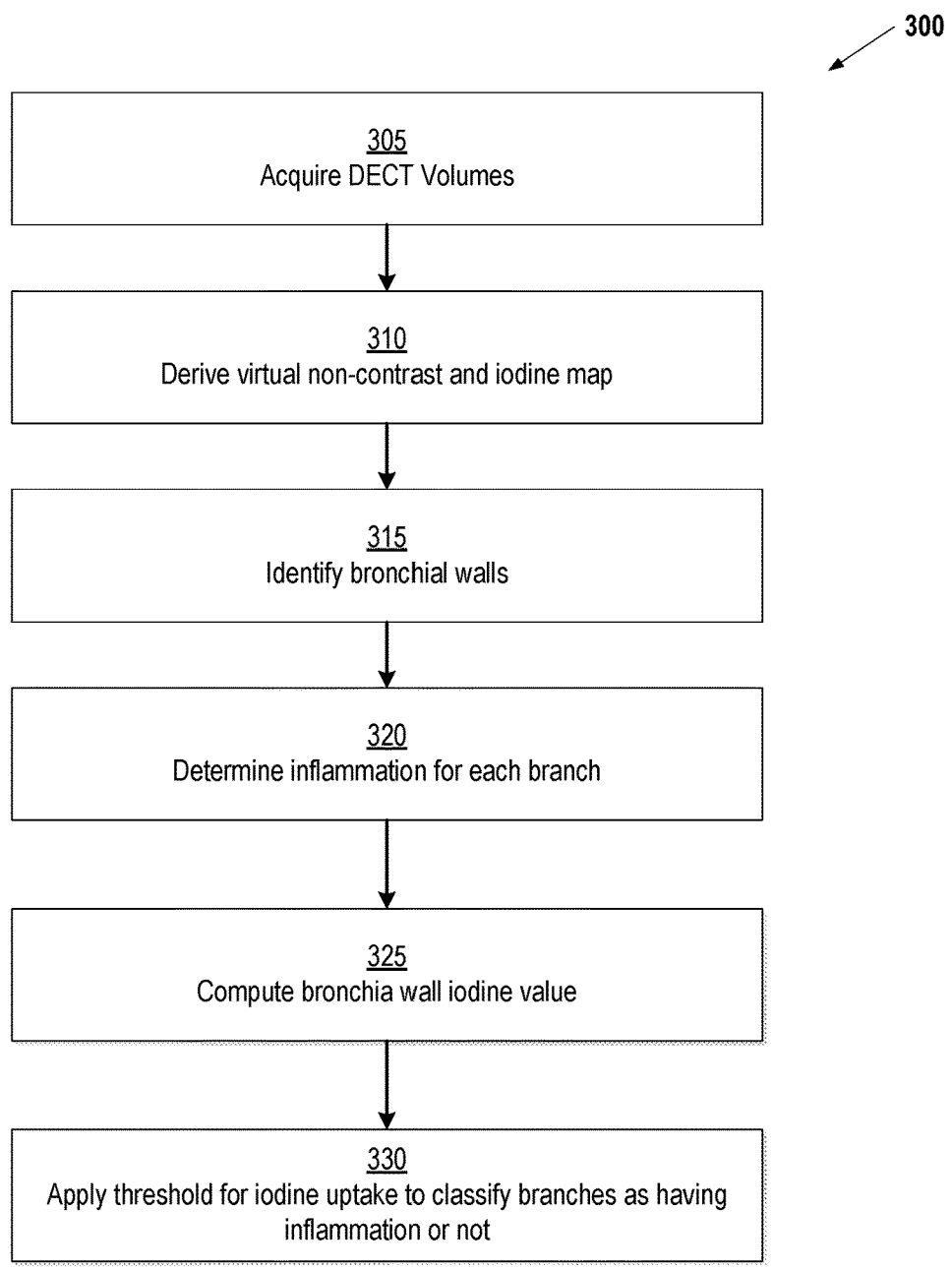
FIG. 3 provides a method for detection of inflamed bronchial walls, according to some embodiments.

FIG. 3 provides a method 300 for detection of inflamed bronchial walls, according to some embodiments. A step 305, a DECT acquisition is performed. In principle, this can be same CT acquisition that is performed at step 105 of the method 100 illustrated in FIG. 1. A typical DECT acquisition produces two volumes, one at low energy (e.g. 80 kV) and one at high energy (e.g. 140 kV). These volumes are referred to herein as $V_{low}$ and $V_{high}$, respectively. These values may be used to determine an average voltage $V_{average}$. For example, the standard software provided on a Siemens workstation with a Dual Energy module allows for the creation of a volume that simulates an acquisition at an average voltage $V_{average}$, (e.g. 120 kV) by taking a weighted average of $V_{low}$ and $V_{high}$.

In this example, it is assumed that the patient has been given iodinated contrast. Based on this contrast and the DECT volumes, at step 310, a virtual non-contrast (VNC) volume, $V_{vnc}$, and an "iodine map" volume, $V_{iodine}$, may also be derived from the original acquisitions $V_{low}$ and $V_{high}$. The iodine map shows for every voxel, the computed amount of iodine present at the location in the body. The VNC image depicts how the acquisition would have looked without contrast agent, and is typically computed by subtracting the iodine map from the post-contrast image. It should be noted that the methods described above for deriving volumes $V_{average}$, $V_{vnc}$, and $V_{iodine}$ are exemplary and other methods may be employed in other embodiments.

Next, at step 315, the bronchial walls are identified. The inner and outer airway wall contours at each point on the centerline are automatically computed for each branch b∈B.

All voxels that fall between those contours form the locations within the bronchial walls. These locations may be stored in the form of a mask $M_{airway}$, which has the same size as the 3D input volume, and where every voxel has a value to indicate whether it is inside a bronchial wall or not. Alternatively, for each branch b, a list of all the voxels $L_b$ that are in the wall of that branch may be stored.

At step 320, the inflammation as measured by the iodine uptake is determined for each branch b using the locations that form the wall of each branch (from either the map $M_{airway}$ or the list $L_b$) and samples the value in the Iodine Map $V_{iodine}$. Then, at step 325, given the set of iodine values, a function is computed such as the arithmetic mean, median, maximum, etc. to compute a bronchial wall iodine value for the entire branch b; this yields $v_b$. A threshold for the iodine uptake (e.g., 5 HU) is set so that branches can be classified as having inflammation or not at step 330. This results in a binary indicator $i_b$ that indicates whether the wall b is inflamed. In some embodiments, $i_b$ is binary, while $i_b$ in other embodiments can take on a range of values to indicate greater or lesser degrees of inflammation.

Given the computed tree T with branches B, we have for each branch b∈B an indication $t_b$ of whether it has abnormal thickening, and an indication $i_b$ of whether it has abnormal inflammation. The interactive display presents to the user an indication of whether a wall is (1) thickened without inflammation, (2) thickened with inflammation, (3) inflamed without thickening, or normal. The different values may be differentiated using coloring, shading, or another visual indicator on the display.

FIG. 4 provides an example of the color display map that may be employed in some embodiments to distinguish between thickened walls with and without inflammation. Because this table is presented herein in black and white, the color labels are shown in brackets below each designation of inflammation and thickening. It should be understood that, in practice, colors corresponding to these labels would be used for quick visual identification of the presented results.

Note, that for completeness, FIG. 4 includes a coloring to indicate walls that have inflammation but no thickening. In practice, this condition is rare. Thus most renderings will show only 3 colors: red to indicate thickening with inflammation, green to indicate thickening without inflammation, and blue to indicate normal airway walls. It is also possible to create a table with additional rows and/or columns to indicate greater or lesser degrees or inflammation and greater or lesser degrees of thickening. This would be used in the case that $t_b$ and/or $i_b$ are multi-valued rather than binary. This would allow the physician, for example, to visualize thickened walls with greater or lesser degrees of inflammation.

Given a lookup table similar to the example in FIG. 4, the system presents these indicators of disease through multiple interactive displays. Multiplanar Reconstructions (MPRs) indicating the axial, coronal and sagittal views show the original CT values. Voxels corresponding to the detected bronchial wall locations have a semi-transparent overlay of the color indicated in FIG. 4 (or other chosen color scheme). Thus as physicians scroll through planar views of the data, they can quickly identify which walls have thickening with or without inflammation, according to whether the walls appear red vs. green.

In some embodiments, an interactive 3D rendering of the bronchial tree may also be presented, where each branch is colored according to the table in FIG. 4 (or other chosen color scheme). In this way, the system presents an overall view of the bronchial tree. This view allows physicians to quickly determine the presence and extent of wall thickening; it also allows them to determine whether it occurs primarily in the upper vs. lower lobes, or right vs. left sides. A predominance of red indicates most thickened walls also exhibit inflammation, whereas a predominance of green overlay indicates that the thickened walls do not have inflammation. A predominance of blue indicates that most of the airway walls are normal. Through the use of differing colors, physicians can rapidly appreciate whether the thickening is accompanied by inflammation in the majority of branches, and whether the inflammation has a differential distribution such as upper vs. lower or right vs. left.

In some embodiments, an interactive "tour" mode is provided to take the physician rapidly from one location to another, corresponding to walls exhibiting thickening and/or inflammation. For example, if the physician pushes forward/backwards interactive components (e.g., arrow buttons) on the interface, the system may present a magnified local view of the next (or previous) airway. This tour cycles through a list of airways that exhibit thickening. Additionally (or alternatively), the interface may include radio buttons that allow the physician request to cycle through a list of thickened walls with or without inflammation (e.g., red vs. green). It should be noted that these interactions are exemplary and other techniques can be used such as mouse, menus or different keyboard presses in other embodiments.

Figure 5:
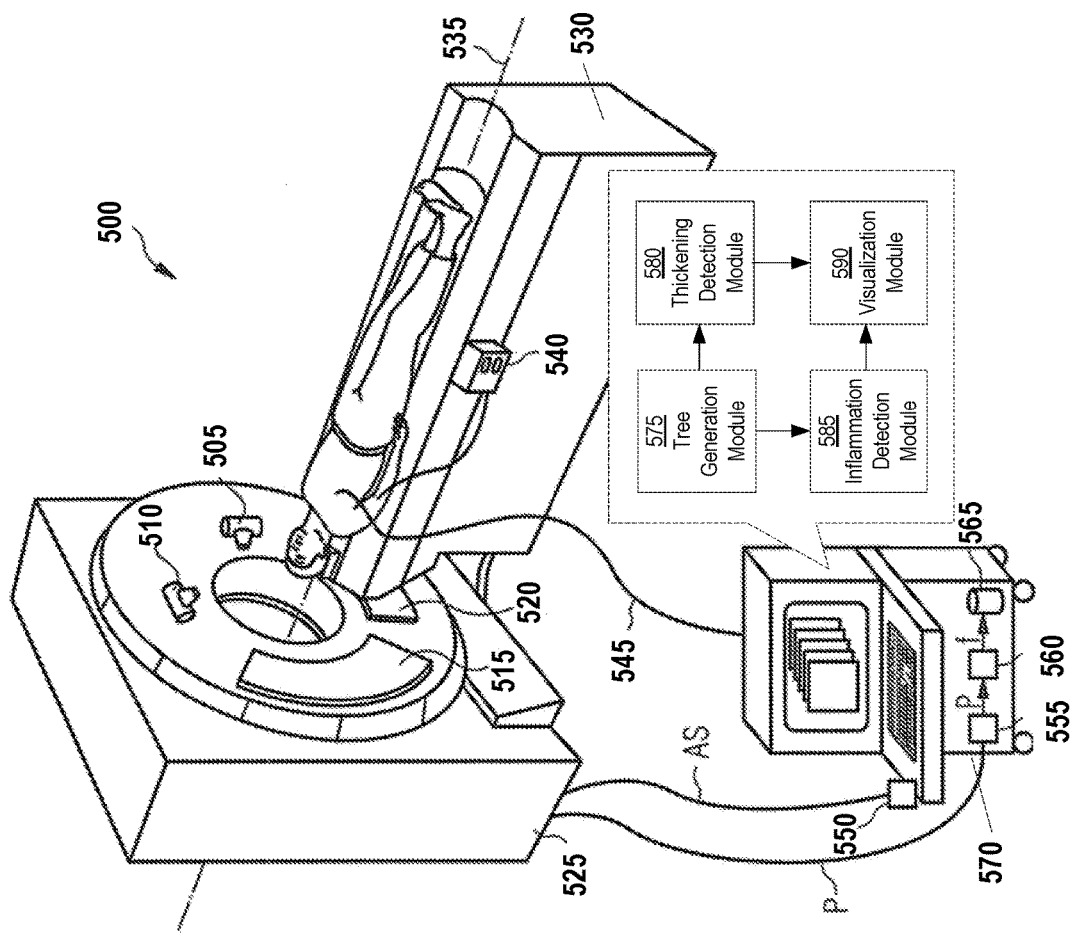
FIG. 5 illustrates an exemplary CT system within which embodiments of the invention may be implemented.

FIG. 5 illustrates an exemplary CT system 500 within which embodiments of the invention may be implemented. Contained in the gantry housing 525 is a closed gantry (not shown in FIG. 5) on which a first X-ray tube 505 having an oppositely disposed detector 515 is arranged. Optionally, a second X-ray tube 510 having an oppositely disposed detector 520 is arranged in the CT system shown here, thereby enabling a higher time resolution to be achieved by virtue of the additionally available radiation source/detector combination, or, if different X-ray energy spectra are used in the radiation source/detector systems, also enabling DECT examinations to be performed.

The CT system 500 additionally has a patient table 530 on which a patient can be moved during the examination along a system axis 535, also referred to as the z-axis, into the measurement field, wherein the scanning itself can take place both as a pure circular scan without patient advance exclusively in the examination region of interest. In this scenario the X-ray source 505 or 510 rotates around the patient in each case. In parallel therewith the detector 515 or 520 co-rotates with the X-ray source 505 or 510, respectively, in order to acquire projection measured data which are then used to reconstruct sectional images or slices. As an alternative to a sequential scan, in which the patient is moved incrementally through the examination field between the individual scans, it is of course also possible to perform a spiral scan, in which, in the course of the circumferential scanning by means of the X-ray radiation, the patient is moved continuously along the system axis 535 through the examination field between X-ray source 505 or 510 and detector 515 or 520 respectively. With a spiral scan, the movement of the patient along the axis 535 and the simultaneous rotation of the X-ray source 505 or 510 cause the X-ray source 505 or 510 to follow a helical path relative to the patient during the measurement.

The CT system 500 is controlled by way of a control and computing unit 570 having computer program code residing in a memory. Acquisition control signals AS can be transmitted from the control and computing unit 570 via a control interface 550 in order to control the CT system 500 in accordance with specific measurement protocols.

The projection measured data p (also referred to below as raw data) acquired by the detector 515 or 520 are passed to the control and computing unit 570 via a raw data interface 555. Following suitable preprocessing where appropriate, said raw data p are then processed further in an image reconstruction component 560. In the present example, an embodiment of the image reconstruction component 560 is implemented in the control and computing unit 570 in the form of software on a processor, e.g. in the form of one or more of the computer program codes. The image data f reconstructed by the image reconstruction component 560 are then stored in a memory 565 of the control and computing unit 570 and/or output in the conventional manner on the monitor of the control and computing unit 570. The data can also be fed via an interface (not shown in FIG. 5) into a network connected to the CT system 500, a radiological information system (RIS) for example, and stored in a mass storage device that is accessible there or output as images.

In addition, the control and computing unit 570 can also perform the function of an electrocardiogram (ECG), with a cable 545 being used between patient and control and computing unit 570 in order to derive the ECG potentials. In addition, the CT system 500 shown in FIG. 5 also has a contrast agent injector 540 via which contrast agent can additionally be injected into the patient's bloodstream so that the vessels of the patient, in particular the ventricles of the beating heart, can be visualized more clearly. Furthermore this also affords the possibility of performing perfusion measurements, to which the proposed method is likewise suited. Finally, the use of contrast allows the possibility of computing the virtual non-contrast (VNC) volume, $V_{vnc}$, and an "iodine map" volume, $V_{iodine}$ described above.

The computing unit 570 includes a plurality of modules for visualizing airway wall abnormalities, according to the techniques described herein. In the example of FIG. 5, four example modules 575, 580, 585, and 590 are shown. These modules 575, 580, 585, and 590 may each be executable applications or, alternatively, they may be part of a single executable application. The Tree Generation Module 575 generates the tree model and provides it a Thickening Detection Module 580 which detects abnormal thickening of bronchial walls as described above with reference to FIG. 1. The tree model is also provided to an Inflammation Detection Model 585 which detects inflammation of the bronchial walls using the techniques described above with reference to FIG. 3. The results generated by the Thickening Detection Module 580 and Inflammation Detection Module 585 are provided to a Visualization Module 590 which, in turn, generates a visualization of any thickening and/or inflammation abnormalities on the display of the computing unit 570.

It should be noted that the computing environment illustrated in FIG. 5 is merely exemplary. In other embodiments, more specialized computing devices may be employed, possibly in clinical settings remote from the scanner itself. For example, DECT imaging data can be acquired using the scanner and stored. Then, at some later period, a computer can retrieve the data and present the visualizations described herein.

In some embodiments, the computing unit which generates the visualization of airway wall abnormalities is a parallel computing environment which includes a plurality of central processing units (CPUs) and/or graphical processing units (GPUs) which are configured to perform some of the visualization processing in parallel. For example, as described above with reference to FIGS. 1 and 3, the thickening and inflammation calculations are performed, in part, on a branch-by-branch basis. In embodiments, where parallel computing is available, calculations on multiple branches may be performed in parallel. Thus, thickening and inflammation calculations may be performed for two different branches simultaneously. Alternatively (or additionally), the thickening and inflammation calculations for a single branch may be performed in parallel across two or more processors.

The computing unit used to implement the techniques described herein may include at least one computer readable medium or memory for holding instructions programmed according to embodiments of the invention and for containing data structures, tables, records, or other data described herein. The term "computer readable medium" as used herein refers to any medium that participates in providing instructions to the processor(s) of the computing unit for execution. A computer readable medium may take many forms including, but not limited to, non-volatile media, volatile media, and transmission media. Non-limiting examples of non-volatile media include optical disks, solid state drives, magnetic disks, and magneto-optical disks, such as a hard disk or a removable media drive. Non-limiting examples of volatile media include dynamic memory, such as system memory. Non-limiting examples of transmission media include coaxial cables, copper wire, and fiber optics, including the wires that make up the system buses used by the computing unit. Transmission media may also take the form of acoustic or light waves, such as those generated during radio wave and infrared data communications.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for visualizing airway wall abnormalities, the method comprising:
   acquiring Dual Energy Computed Tomography (DECT) imaging data comprising one or more image volumes representative of a bronchial tree;
   deriving an iodine map using the DECT imaging data;
   segmenting the bronchial tree from the one or more image volumes;
   generating a tree model representative of the bronchial tree;
   for each branch of the bronchial tree, using the tree model to determine an indicator of normal or abnormal thickness for the branch;
   identifying locations corresponding to bronchial walls in the bronchial tree using the tree model;
   for each branch of the bronchial tree, using the locations corresponding to bronchial walls in the bronchial tree and the iodine map to determine an indicator of normal or abnormal inflammation as measured by iodine uptake on the branch; and
   presenting a visualization of the bronchial tree with visual indicators at each of the locations corresponding to bronchial walls indicating whether a bronchial wall is thickened, inflamed, or both thickened and inflamed.

2. The method of claim 1, wherein the tree model is used to determine the indicator of normal or abnormal thickness for the branch by:
   using the tree model to segment inner and outer walls of each branch in the bronchial tree;
   computing local wall thickness for each branch based on the branch's corresponding inner and outer walls;
   computing an overall wall thickness for each branch of the bronchial tree based on the local wall thickness computed for each branch; and
   for each branch of the bronchial tree, using the overall wall thickness across the branch to determine the indicator of normal or abnormal thickness for the branch.

3. The method of claim 2, wherein the overall wall thickness comprises a mean wall thickness computed using the local wall thickness computed for each branch.

4. The method of claim 2, wherein the overall wall thickness corresponds to a maximum wall thickness among the local wall thickness computed for each branch.

5. The method of claim 2, wherein each branch in the bronchial tree corresponds to a generation number and the indicator of normal or abnormal thickness for the branch is determined by:
   designating the branch as having abnormal thickness if the overall wall thickness is above a predetermined threshold value corresponding to the generation number.

6. The method of claim 2, wherein the indicator of normal or abnormal thickness for the branch is determined by:
   identifying an artery that is adjacent to the branch using the DECT imaging data;
   determining the diameter of the artery;
   dividing the overall wall thickness across the branch by the diameter of the artery to yield a ratio for the branch;
   designating the branch as having abnormal thickness if the ratio is above a predetermined threshold value.

7. The method of claim 1, further comprising, for each branch of the bronchial tree:
   determining a set of points form a centerline for the branch;
   computing inner and outer airway wall contours at each point on the centerline of the branch;
   designating voxels in the DECT imaging data that fall between the inner and outer airway wall contours as the locations corresponding to bronchial walls in the bronchial tree.

8. The method of claim 1, wherein the indicator of normal or abnormal thickness for the branch is a binary indicator.

9. The method of claim 1, wherein the indicator of normal or abnormal thickness for the branch providing an indication of degrees of thickening on the branch.

10. The method of claim 1, wherein the indicator of normal or abnormal inflammation for the branch is a binary indicator.

11. The method of claim 1, wherein the indicator of normal or abnormal inflammation for the branch providing an indication of degrees of inflammation on the branch.

12. The method of claim 1, wherein the visualization comprises a Multi-Planar Reconstruction from the DECT imaging data and the visual indicators comprise semi-transparent overlay colors distinguishing between thickened walls with and without inflammation in the bronchial tree.

13. The method of claim 1, wherein the visualization comprises a 3D visualization of the bronchial tree and the visual indicators comprise colors distinguishing between thickened walls with and without inflammation in the bronchial tree.

14. A system for visualizing airway wall abnormalities, the system comprising:
   a Computed Tomography imaging scanner configured to acquire Dual Energy Computed Tomography (DECT) imaging data comprising one or more image volumes representative of a bronchial tree;
   a display; and
   a computing device comprising one or more processors and a non-transitory, computer-readable storage medium in operable communication with the one or more processors, wherein the computer-readable storage medium comprises one or more programming instructions that, when executed, cause the one or more processors to:

derive an iodine map using the DECT imaging data, segment the bronchial tree from the one or more image volumes, generate a tree model representative of the bronchial tree, for each branch of the bronchial tree, use the tree model to determine an indicator of normal or abnormal thickness for the branch, identify locations corresponding to bronchial walls in the bronchial tree using the tree model, for each branch of the bronchial tree, use the locations corresponding to bronchial walls in the bronchial tree and the iodine map to determine an indicator of normal or abnormal inflammation as measured by iodine uptake on the branch, and present a visualization of the bronchial tree on the display with visual indicators at each of the locations corresponding to bronchial walls indicating whether a bronchial wall is thickened, inflamed, or both thickened and inflamed.

15. The system of claim 14, wherein the tree model is used to determine the indicator of normal or abnormal thickness for the branch by:

using the tree model to segment inner and outer walls of each branch of the bronchial tree;

computing local wall thickness for each branch based on the branch's corresponding inner and outer walls;

computing an overall wall thickness for each branch of the bronchial tree based on the local wall thickness computed for each branch; and for each branch, using the overall wall thickness across the branch to determine the indicator of normal or abnormal thickness for the branch.

16. The system of claim 15, wherein each branch of the bronchial tree corresponds to a generation number and the indicator of normal or abnormal thickness for the branch is determined by:

designating the branch as having abnormal thickness if the overall wall thickness is above a predetermined threshold value corresponding to the generation number.

17. The system of claim 15, wherein the indicator of normal or abnormal thickness for the branch is determined by:

identifying an artery that is adjacent to the branch using the DECT imaging data;

determining the diameter of the artery;

dividing the overall wall thickness across the branch by the diameter of the artery to yield a ratio for the branch;

designating the branch as having abnormal thickness if the ratio is above a predetermined threshold value.

18. The system of claim 14, further comprising, for each branch of the bronchial tree:

determining a set of points form a centerline for the branch;

computing inner and outer airway wall contours at each point on the centerline of the branch;

designating voxels in the DECT imaging data that fall between the inner and outer airway wall contours as the locations corresponding to bronchial walls in the bronchial tree.

19. The system of claim 14, wherein the visualization comprises a Multi-Planar Reconstruction from the DECT imaging data and the visual indicators comprise semi-transparent overlay colors distinguishing between thickened walls with and without inflammation in the bronchial tree.

20. The system of claim 14, wherein the visualization comprises a 3D visualization of the bronchial tree and the visual indicators comprise colors distinguishing between thickened walls with and without inflammation in the bronchial tree.

21. The system of claim 19, wherein the visualization further comprises one or more interactive interface components that, when activated, cause the visualization to provide a series of visualizations corresponding to a list of airways that exhibit at least one of thickening or inflammation.

22. A system for visualizing airway wall abnormalities, the system comprising:

a database storing Computed Tomography (CT) imaging data comprising one or more image volumes representative of a bronchial tree;

a parallel computing environment comprising a plurality of processors configured to generate a model of the bronchial tree based on the one or more image volumes;

in parallel for each branch of the bronchial tree, use the model of the bronchial tree to determine (a) an indicator of normal or abnormal thickness for the branch and (b) an indicator of normal or abnormal inflammation for the branch; and present a visualization of the bronchial tree on a display with visual indicators at locations corresponding to bronchial walls indicating whether a bronchial wall is thickened, inflamed, or both thickened and inflamed based on the indicator of normal or abnormal thickness and the indicator of normal or abnormal inflammation determined for each branch.

* * * * *